United States Patent

Manzan et al.

(10) Patent No.: US 9,474,442 B2
(45) Date of Patent: Oct. 25, 2016

(54) APPARATUS FOR INSPECTING THE FUNDUS OF THE EYE

(75) Inventors: Federico Manzan, San Pietro di Feletto (IT); Andrei Plaian, Ponte San Nicolo (IT); Marco D'Aguanno, Padua (IT); Paola Griggio, Padua (IT)

(73) Assignee: CENTERVUE S.P.A., Padua (IT)

(*) Notice: Subject to any disclaimer, the term of this patent is extended or adjusted under 35 U.S.C. 154(b) by 654 days.

(21) Appl. No.: 13/824,108

(22) PCT Filed: Sep. 16, 2011

(86) PCT No.: PCT/EP2011/066141
§ 371 (c)(1),
(2), (4) Date: Mar. 15, 2013

(87) PCT Pub. No.: WO2012/041723
PCT Pub. Date: Apr. 5, 2012

(65) Prior Publication Data
US 2013/0182221 A1 Jul. 18, 2013

(30) Foreign Application Priority Data
Sep. 29, 2010 (IT) .............................. TV2010A0131

(51) Int. Cl.
A61B 3/14 (2006.01)
A61B 3/10 (2006.01)
A61B 3/00 (2006.01)
A61B 3/12 (2006.01)
A61B 3/15 (2006.01)

(52) U.S. Cl.
CPC *A61B 3/12* (2013.01); *A61B 3/152* (2013.01)

(58) Field of Classification Search
USPC ........ 351/206, 200, 205, 209–211, 221–222, 351/246
See application file for complete search history.

(56) References Cited

U.S. PATENT DOCUMENTS

| | | | |
|---|---|---|---|
| 5,355,895 A * | 10/1994 | Hay | A61B 3/103 351/211 |
| 5,844,544 A | 12/1998 | Kahn et al. | |
| 6,027,216 A | 2/2000 | Guyton et al. | |
| 6,064,124 A * | 5/2000 | Inukai | G03G 15/2003 307/114 |
| 2005/0007551 A1 * | 1/2005 | Wakil | A61B 3/107 351/205 |
| 2005/0007552 A1 * | 1/2005 | Fergason | A61B 3/113 351/210 |
| 2006/0200013 A1 | 9/2006 | Smith et al. | |
| 2008/0174734 A1 | 7/2008 | Shimizu et al. | |
| 2009/0002631 A1 | 1/2009 | Campbell et al. | |
| 2011/0001927 A1 | 1/2011 | Kasper | |

FOREIGN PATENT DOCUMENTS

| | | |
|---|---|---|
| DE | 102008000225 B3 | 3/2009 |
| EP | 1452127 A1 | 9/2004 |
| EP | 1864609 A1 | 12/2007 |

OTHER PUBLICATIONS

English translation of Japanese Notice of Reason for Refusal mailed Jun. 30, 2015 in Japanese Patent Application No. 2013-530673 (2 pages).

* cited by examiner

*Primary Examiner* — Dawayne A Pinkney
(74) *Attorney, Agent, or Firm* — Polsinelli PC

(57) ABSTRACT

The present invention relates to an apparatus for inspecting the fundus of the eye, comprising: —lighting means configured to project a light beam for illuminating the retina of one eye; and —an optical path comprising one or more lenses configured to optically conjugate the retina with a receiving surface of acquisition means configured to acquire one or more images of the retina; and —a beam splitter device configured to divert a part of the light, which is reflected by the retina and directed towards said acquisition means, towards first photosensitive elements; and —a control unit operatively associated with said first photosensitive elements, said acquisition means and said lighting means, said control unit deactivating said lighting means when the light energy received from said first photosensitive elements overcomes a predefined threshold value; and —first LED devices configured to project light targets onto the retina, which the patient must stare to keep the eye still during the examination. The mentioned first photosensitive elements and first LED devices are arranged together in a single integrated optical unit configured to receive light from the retina and to project light onto the retina through said beam splitter device.

7 Claims, 8 Drawing Sheets

APPARATUS FOR INSPECTING THE FUNDUS OF THE EYE

CROSS REFERENCE TO RELATED APPLICATIONS

Figure 1:
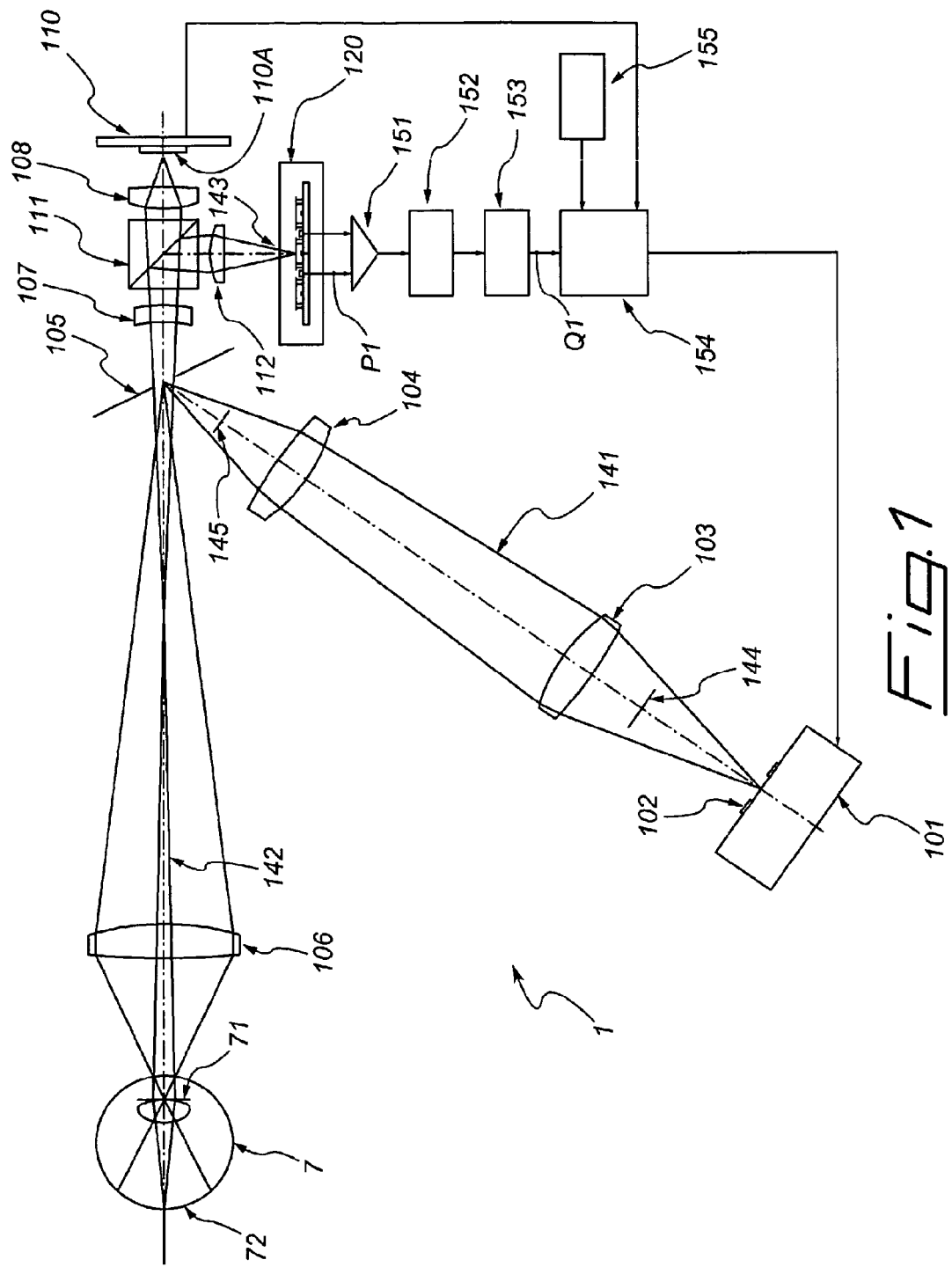

This application is a National Phase filing under 35 U.S.C. §371 of PCT/EP2011/066141 filed on Sep. 16, 2011; and this application claims priority to Application No. TV2010A000131 filed in Italy on Sep. 29, 2010 under 35 U.S.C. §119; the entire contents of all are hereby incorporated by reference.

The present invention relates to an apparatus for inspecting the fundus of the eye.

The use of apparatus for inspecting the fundus of the eye, commonly referred to as "fundus camera", is widely known.

These devices optically conjugate the patient's eye pupil with a lighting device, so that the retina is illuminated with a beam of light that has an annular section at the pupil level.

The light reflected by the retina is collected through the central portion of the pupil, by appropriate acquisition means necessary to enable the observation of the retina and to carry out the shooting thereof.

In apparatus for inspecting the fundus of the eye, means for adjusting the light exposure of the acquisition means for taking pictures of the retina are generally arranged.

These adjusting means control the operation of the device for lighting the fundus camera to adjust the amount of light received by the acquisition means and obtain a homogeneous light exposure on all pictures taken, regardless of the reflectivity of the retina of the patient examined.

U.S. Pat. No. 4,429,970 and U.S. Pat. No. 4,600,525 describe some known types of apparatus for the inspection of the fundus.

In such devices, light exposure adjustment means include a beam splitter device, i.e. an optical device capable of separating a light beam received in input and diverting a part thereof towards a desired direction.

The beam splitter device is positioned along the optical path between the retina and the acquisition means and diverts a portion of light coming from the retina to a light sensor.

The detection signals generated by the light sensor are used to regulate the operation of the fundus camera lighting device to maintain an optimal value for the amount of light received by the acquisition means.

The traditional solutions described in the above patents have some drawbacks.

In such apparatus, in fact, it is quite difficult to use low cost light sensors.

The amount of light reflected by the retina is very low and the sensitivity of the light sensor must necessarily be very high, since the light sensor only receives a small part of the light reflected by the retina.

In the low cost light sensors currently available (photodiodes and phototransistors), the sensitivity is strongly temperature dependent, for low levels of light power in input.

If temperature variations are neglected during the measurement process, as occurs in the apparatus described in the above patents, unacceptable measurement errors may occur.

Of course, the need to use high performance light sensors results in an increase in the overall costs of inspection apparatus.

Often, in the apparatus for inspecting the eye fundus there are arranged means for projecting light targets onto the patient's retina. Such light targets are stared at by the patient to maintain the eye steady in a predetermined position during the examination of the retina.

In traditional inspection apparatus, to project said light targets onto the retina, it is necessary to use additional beam splitter devices to insert light beams in the optical path between the retina and the acquisition means or in the optical path between the lighting device and the retina.

The presence of additional beam splitter devices is disadvantageous because it increases the overall cost of the fundus camera and optically interferes with the light beams received by the acquisition means, reducing the contrast and quality of the retina pictures.

This latter problem might be overcome by introducing removable optical elements during the shooting of the retina. This solution, however, makes the structure of the fundus camera even more complex and, consequently, more cumbersome and expensive to produce industrially.

The main task of the present invention is to provide an apparatus for the inspection of the eye fundus which overcomes the disadvantages the prior art, shown above.

Within the scope of such task, one object of the present invention is to provide an inspection apparatus that allows effectively regulating the light exposure of the acquisition means intended to shoot the retina and, at the same time, allows projecting light targets on the retina without interfering unnecessarily on the optical path of light towards said acquisition means.

A further object of the present invention is to provide an inspection apparatus that has great compactness, simple design and small overall dimensions.

A further object of the present invention is to provide an inspection apparatus that can be easily manufactured on an industrial scale at competitive costs.

The present invention thus provides an apparatus for the inspection of the eye fundus, according to claim 1, given below.

In a general definition thereof, the apparatus for the inspection of the eye fundus includes lighting means, configured to project a light beam to illuminate the retina of the patient, and acquisition means, configured to receive the light reflected by the retina, at a receiving surface, and acquire one or more images of the retina.

In the apparatus, according to the invention, an optical path is provided, which comprises one or more lenses configured to optically conjugate the retina with said receiving surface.

The apparatus, according to the invention comprises a beam splitter device suitable for diverting a portion of the light, which is reflected by the retina and directed towards the acquisition means, towards first photosensitive elements.

The apparatus, according to the invention, includes a control unit operatively associated with the first photosensitive elements, acquisition means and lighting means. In operation, said control unit deactivates said lighting means when the light energy received from said first photosensitive elements overcomes a predefined threshold value.

The apparatus, according to the invention comprises also first LED devices configured to project light targets onto the retina, which the patient must stare to keep the eye still during the examination.

According to the invention, said first photosensitive elements and first LED devices are arranged together in a single integrated optical unit configured to receive light from the retina and to project light onto the retina through said beam splitter device.

Said integrated optical unit, operatively associated with the optical path between the retina and the acquisition means by means of a single beam splitter device, is advantageously able to simultaneously perform the functions of measuring the amount of light reflected by the retina and projecting light setting targets onto the retina.

Such a solution allows minimizing the interference with the light beam that creates the image of the retina on the acquisition means, considerably improving the quality and contrast of the images taken by the acquisition means.

The integration of the first photosensitive element and the first LED devices in a single structural component allows limiting weight and overall dimensions of the inspection apparatus.

According to a preferred embodiment of the present invention, the integrated optical unit is provided with a thermal calibration unit that includes at least one second LED device and at least one second photosensitive element.

Such thermal calibration unit allows the control unit to effectively compensate the effects of any changes in the operating temperature of the first photosensitive elements on the light exposure adjustment operations.

Further aspects of the present invention relate to some calibration procedures automatically executable by the control unit.

Such calibration procedures ensure ease of implementation, good accuracy and repeatability as regards the setup operations of the inspection apparatus.

Figure 2:
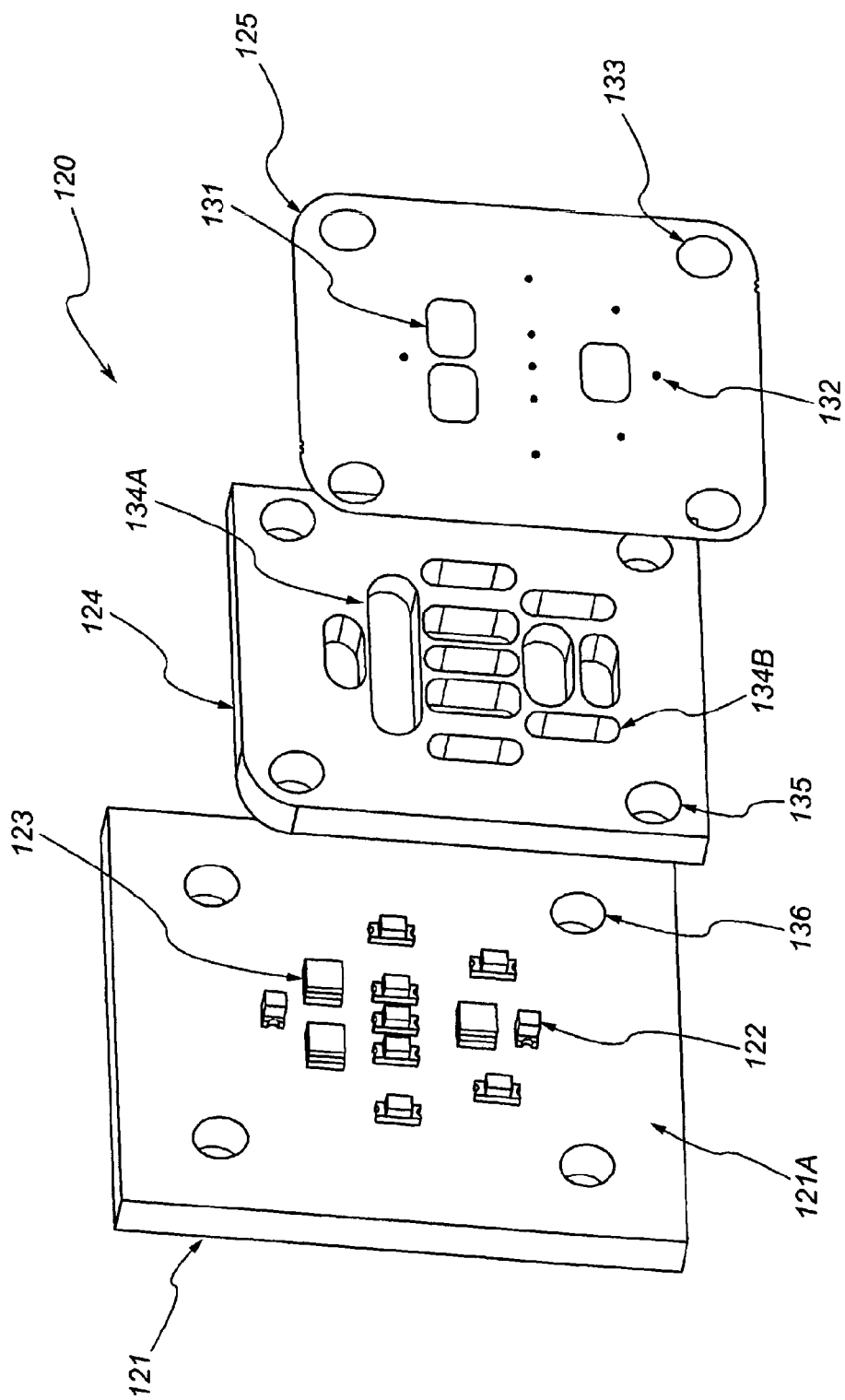
Figure 3:
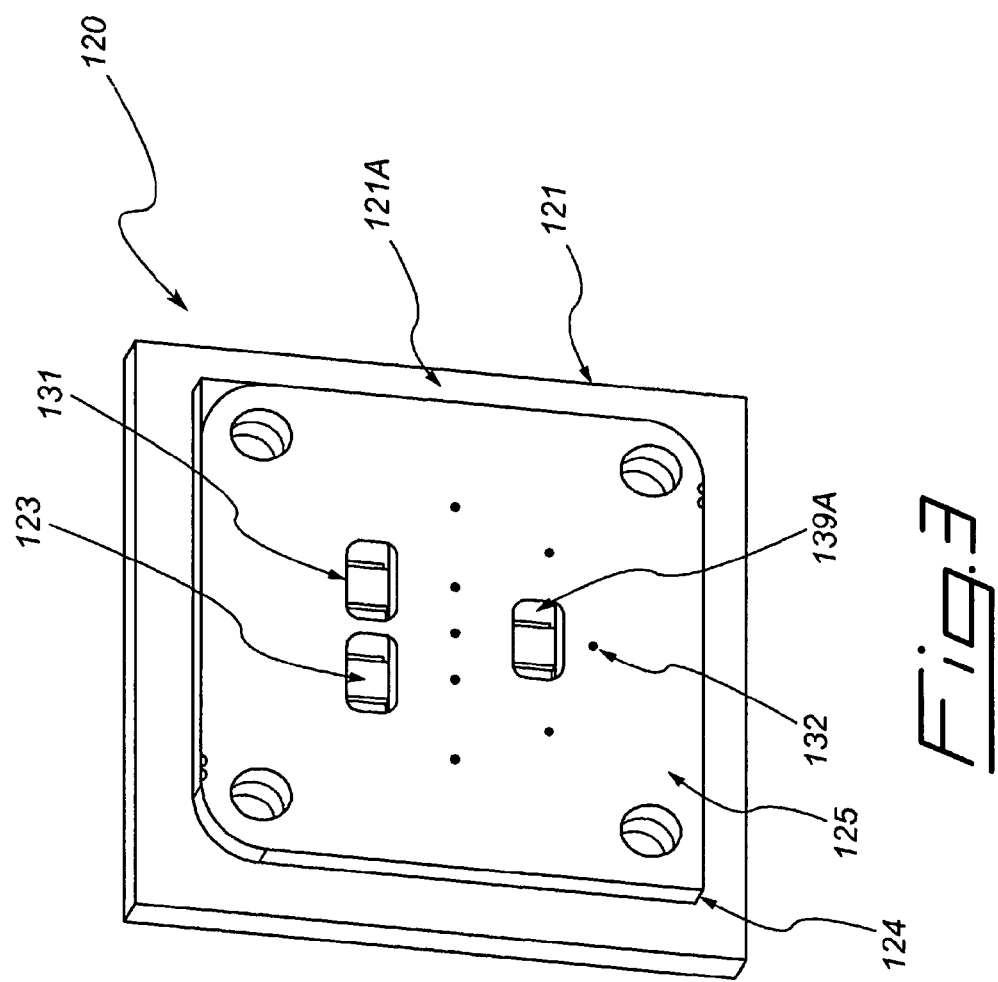
Figure 4:
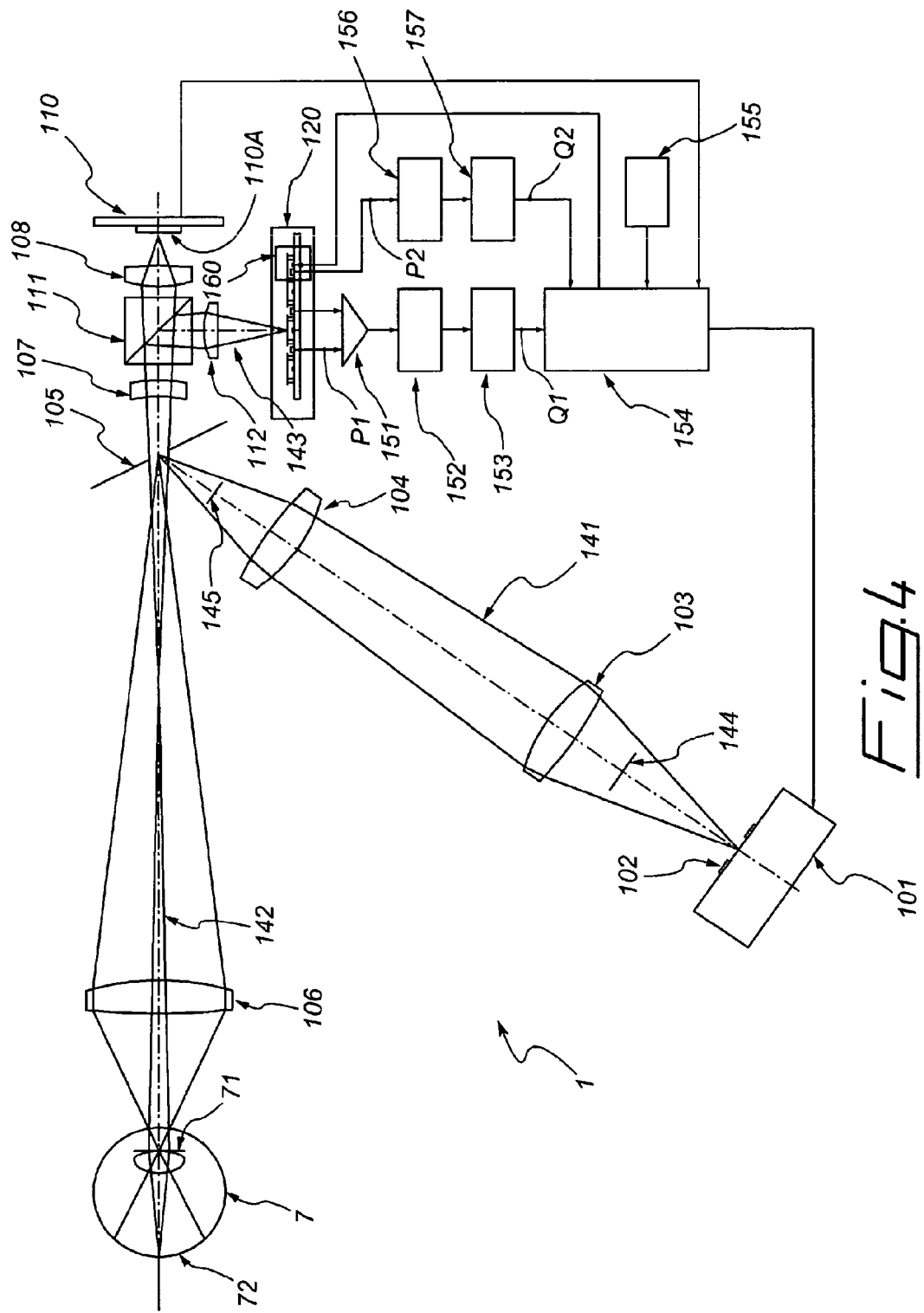
Figure 5:
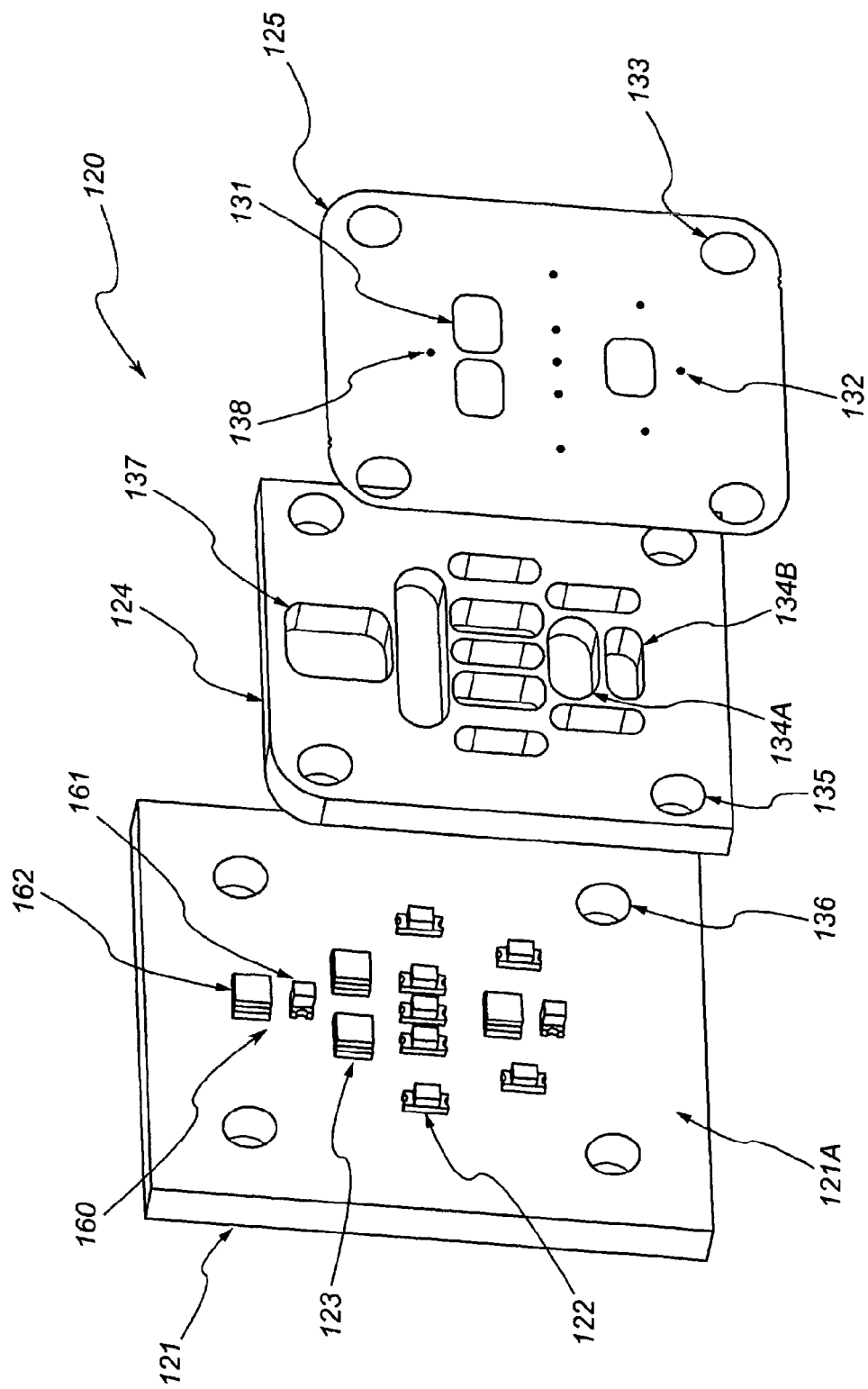
Figure 6:
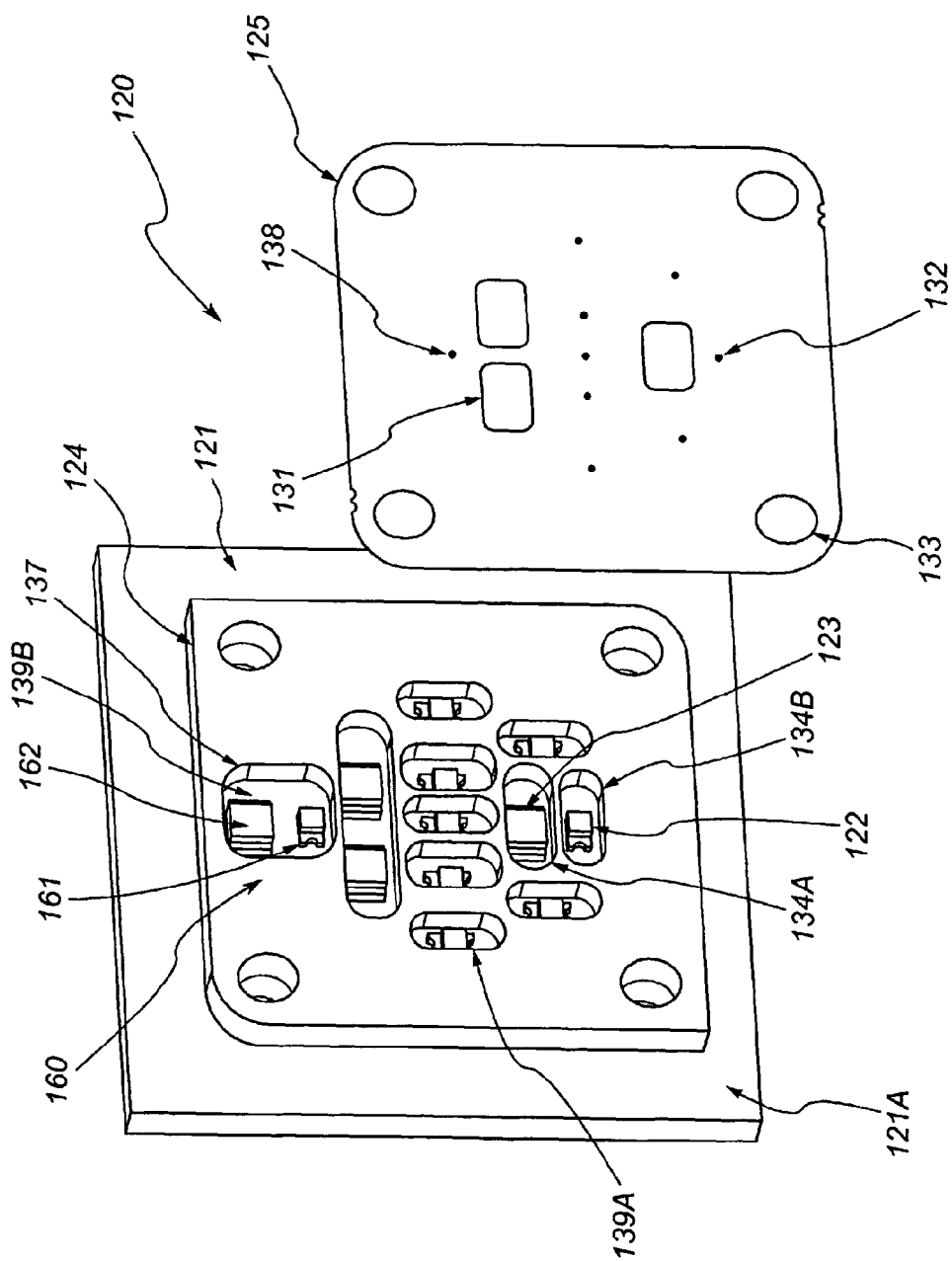
Figure 7:
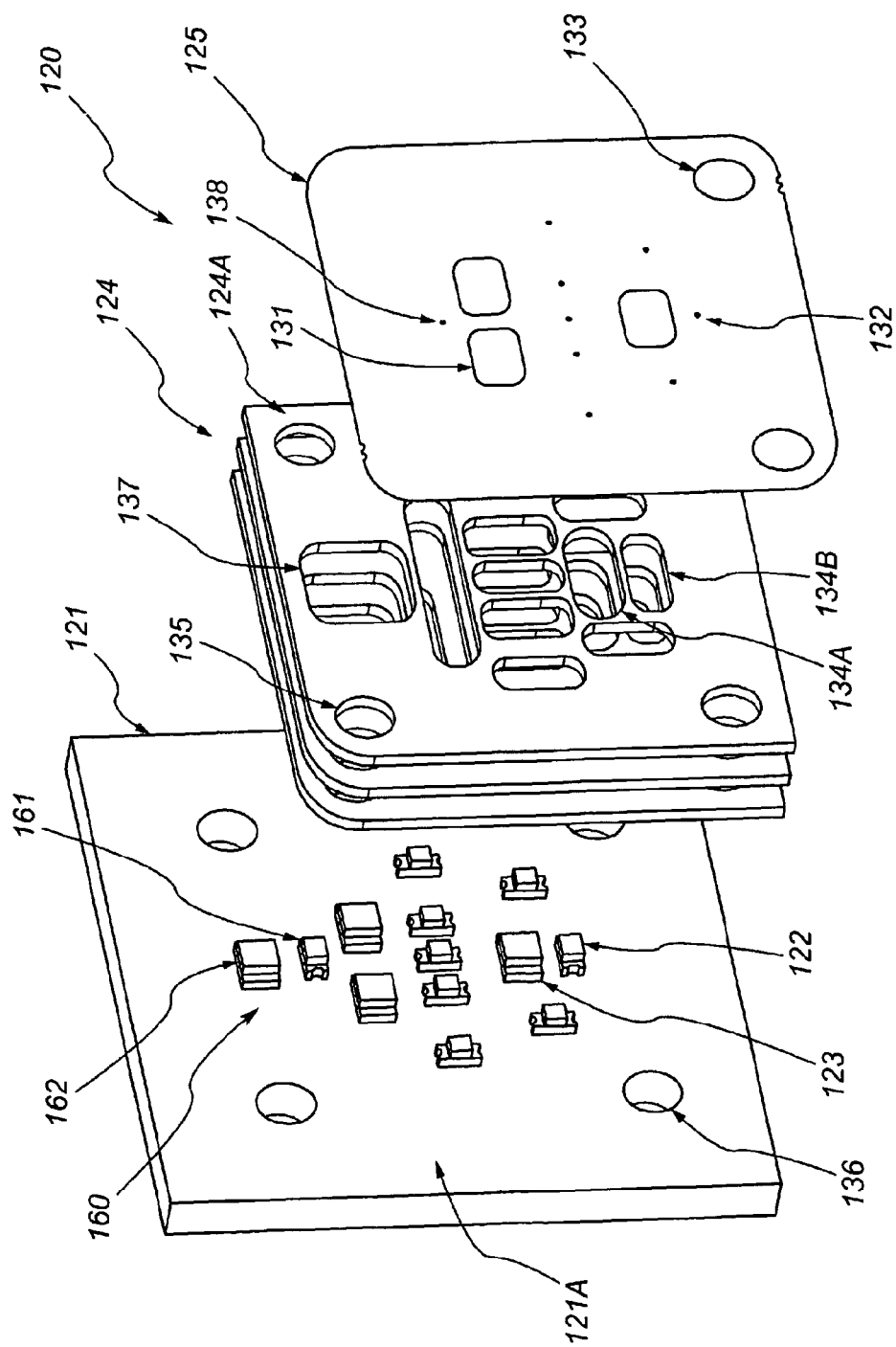
Figure 8:
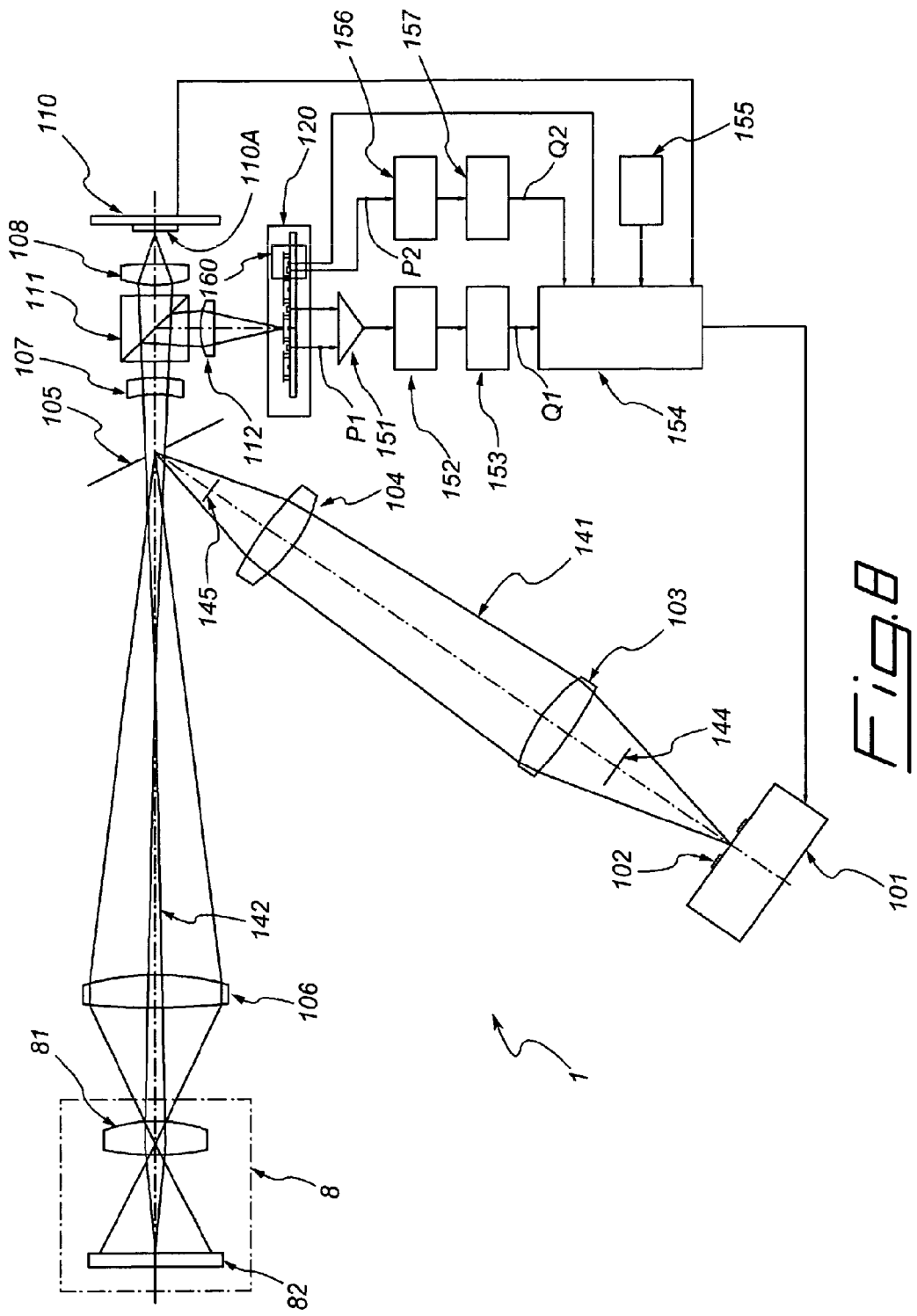

Further features and advantages of the apparatus for inspecting the eye fundus, according to the invention, will appear more clearly with reference to the description given below and to the attached figures, provided by way of a non-limiting illustration only, wherein:

FIG. 1 schematically shows the apparatus for inspecting the eye fundus, according to the invention, in an embodiment thereof; and FIGS. 2-3 show schematic perspective exploded and assembly views of the optical unit integrated in the inspection apparatus of FIG. 1; and FIG. 4 schematically shows the inspection apparatus, according to the invention, in a further embodiment thereof; and FIGS. 5-6 schematically show perspective exploded views of the optical unit integrated in the inspection apparatus of FIG. 4; and FIG. 7 schematically shows an exploded perspective view of a further embodiment of the optical unit integrated in the inspection apparatus of FIG. 4; and FIG. 8 schematically shows the inspection apparatus of FIG. 4 during a calibration process.

With reference to the above figures, the present invention relates to an apparatus for inspecting the eye fundus 1.

The apparatus 1 comprises lighting means 101 suitable for projecting a light beam 141 for illuminating retina 72 of eye 7 of the patient.

The lighting means 101 include, preferably, an illuminator provided with an annular zone 102 whereat the light beam 141 is emitted.

Preferably, through a lens system 103 and 104, light 141 emitted by the lighting means 101 is collimated in an area substantially coinciding with the center of a perforated mirror 105.

Light 141 is then reflected by mirror 105 and collimated with a lens 106 in a zone located approximately in the plane of pupil 71 to finally reach retina 72, illuminating it.

In the optical path described above there are preferably present a first opaque disk 144 and a second opaque disk 145 suitable for blocking the light that could generate reflections on the eye crystalline and cornea 7, respectively.

The apparatus 1 comprises also an optical path comprising the lenses 106, 107, 108 configured to optically conjugate the retina 72 with a receiving surface 110A of acquisition means 110 to acquire one or more images of the retina.

Light 142 reflected by retina 72 passes through the central zone of pupil 71 and is directed through lens 106, towards the hole of mirror 105.

Subsequently, the light beam 142 is collimated with a lens formed by the lens groups 107 and 108 at the acquisition means 110.

Preferably, at least one lens of the lens group 107 is movable axially to achieve the focus of retina 72 at the acquisition means 110.

The acquisition means 110 are made of, for example, CCD or C-MOS sensors of a digital camera. They receive light 142, at the receiving surface 110A, and advantageously allow the observation and shooting of retina 72.

In the section of the optical path between the lens group 107 and the acquisition means 110, the apparatus 1 includes a beam splitter device 111 configured to divert a portion 143 of the light beam 142 reflected by the retina and directed towards the acquisition means 110.

The beam splitter device 111 directs said light portion 143 towards first photosensitive elements 123 consisting of, for example, photodiodes or phototransistors.

The apparatus 1 has a control unit 154 operatively associated with the first photosensitive elements 123, the acquisition means 110 and the lighting means 101.

The control unit 154 includes comprises digital processing means (not shown) for executing programs, software modules or procedures.

The control unit 154 may be operatively associated with a human machine interface 155 for entering manual commands or performing configuration or programming operations.

The apparatus 1 comprises also first LED devices 122 configured to project light targets onto the retina, which the patient must stare to keep the eye still during the examination.

According to the invention, the first photosensitive elements 123 and the first LED devices 122 are arranged together in a single integrated optical unit 120 configured to receive light 143 from the retina and to project light onto the retina through the beam splitter device 111.

The optical unit 120 is advantageously positioned in a zone substantially optically conjugated with retina 72 and it simultaneously performs a function of measuring the light exposure of the acquisition means 110, that is, the amount of light reflected by the retina to the acquisition means 110, and a function of projection of light targets on the retina.

A group of lenses 112 is preferably positioned between unit 120 and the beam splitter device 111 to ensure an optimal distance between these components and/or obtain optimal dimensions of the image of the retina at the plane where the integrated optical unit 120 is.

Preferably, the integrated optical unit 120 includes a support element 121, which has a mounting surface 121A whereon first photosensitive elements 123 and the first LED devices 122 are arranged.

Advantageously, the support element 121 consists of a printed circuit board, on a surface 121A whereof there are mounted the electronic devices 123 and 122.

The optical unit 120 preferably includes a first mask 124 superimposed on the mounting surface 121A of the support element 121 and in contact with the latter.

Mask 124 includes first and second through openings 134A and 134B.

Openings 134A are designed to allow the photosensitive elements 123 to receive light from the beam splitter device 111, while shielding the photosensitive elements 123 from the light from other sources, for example from the light coming from other LED devices and/or from the outside.

The second through openings 134B, on the other hand, are arranged to allow the LED devices 122 to emit light towards the beam splitter device 111 and optically shield the LED devices 122 with respect to each other and with respect to the photosensitive elements 123.

It should be noted that openings 134A and 134B, when mask 124 is resting on the mounting surface 121A, define seats 139A suitable for respectively seating devices 123 or devices 122 (see FIGS. 3 and 6).

Such seats are laterally closed and open towards the beam splitter device 111, to allow the passage of light radiation only from/to the beam splitter device 111 and shield light from light sources external to said seats.

Preferably, the integrated optical unit 120 also includes a second mask 125 superimposed on the first mask 124 and positioned in a plane optically conjugate with retina 72.

Advantageously, the mask 125 includes third through openings 131 arranged at the photosensitive elements 123 and at least partially superimposed to the first through openings 134A, so as to allow the photosensitive elements 123 to receive light from the beam splitter device 111.

The through openings 131 are relatively large so that a sufficient amount of light reaches the photosensitive elements 123 in the time interval in which the retina is illuminated and the acquisition means 110 acquire images of the same retina.

The mask 125 also includes fourth through openings 132 arranged at the LED devices 122 and at least partially superimposed on the second through openings 134B so as to enable the LED devices 122 to emit light toward the beam splitter device 111.

The through openings 132 are advantageously formed by small holes wherethrough the light emitted by the LED devices 122 can pass, forming light beams directed towards the beam splitter device and diverted by the latter towards the eye 7.

Such light beams project light targets (such as small bright disks) on retina 72 that the patient must stare to keep the eye still during the examination.

The LED devices 122 may be activated individually, in order to project only the light target related to a particular position for the patient's eye on the retina.

Advantageously, the board 121 and the masks 124, 125 include centering holes 136, 135 and 133 which seat mounting screws (not shown) designed to clamp the board 121 and the masks 124, 125 sandwich-wise and fix the optical unit 120 on a support structure (not shown) of the apparatus 1.

The photosensitive elements 123 generate detection signals P1 indicative of the light power received from the beam splitter device 111.

First electronic means, operatively associated with the photosensitive elements 123 and the control unit 154, are preferably arranged for receiving the detection signals P1 and generating measurement signals Q1 indicative of light energy $E_1$ received by the photosensitive elements 123 and, therefore, indicative of the amount of light received by the retina.

The first electronic means comprise at least an adder 151 for adding together the detection signals P1, an amplifier 152 for amplifying the signal in output from adder 151 and an integrator 153 for integrating the signal in output from the amplifier 152 over time. Of course, the order in which the electronic devices 151-153 operate may be different from that described above.

The measurement signal Q1, indicative of light energy that comes from the retina, is received by the control unit 154 which compares the energy level $E_1$ received from the photosensitive elements 123 with a predefined threshold value $E_{TH}$.

When the light energy $E_1$ received from the photosensitive elements 123 exceeds threshold $E_{TH}$, the control unit 154 generates control signals to deactivate the lighting means 101.

The solution described above has considerable operational advantages.

The integration time of the detection signals P1 is in fact varied according to the reflectivity of the retina.

For example, if the acquisition means shoot a retina with low reflectivity, signal P1 generated by the photosensitive elements 123 has a reduced intensity and a longer integration time is therefore required to reach the predefined threshold $E_{TH}$ and turn off the lighting means 101.

The exposure time to light radiation emitted by the lighting means 101 thus varies inversely proportional to the reflectivity of the retina.

The amount of light that reaches the photosensitive elements 123 therefore remains substantially constant. Since such amount of light is proportional to the amount of light that reaches the acquisition means 110, also the light exposure of the acquisition means 110 is kept constant, allowing pictures with constant light exposure, regardless of the reflectivity of the retina examined.

It should be noted that the first photosensitive elements 123, the first electronic means 151-153 and the control unit 154 constitute means for adjusting the light exposure of the acquisition means 110.

In a preferred embodiment of the present invention, illustrated in FIG. 4, the integrated optical unit 120 includes a thermal calibration unit 160, advantageously formed by a second LED device 161 and a second photosensitive element 162.

The devices 161, 162 are mounted close together on the mounting surface 121A, so that the light emitted by the LED device 161 towards the photosensitive element 162 can easily reach the latter (FIGS. 5-7).

The devices 161, 162 are seated in a same seat 139B defined by the mounting surface 121A and by a fifth through opening 137 obtained in mask 124. The photosensitive element 162 is thus optically shielded from external light sources, other than the photosensitive element 161.

In an embodiment solution not shown, the LED device 161 is independent of the other LED devices 122 used to project light targets on the retina.

Alternatively, as shown in FIGS. 5-6, the LED device 161 can also be used to project a light target on the retina, similar to the LED devices 122.

This solution can be adopted if the space available for mounting the optical unit 120 is reduced and/or it is more appropriate to use different channels to drive the LED devices 122 and 161 by the control unit 154.

Normally, the control unit 154 is capable of sending control signals directly to the first LED device 122 and the second LED device 161. Alternatively, an electronic driving stage can be arranged between the control unit 154 and the above LED devices.

It may be noted that the LED devices 122, the control unit 154 and optionally the LED device 161 constitute means for projecting light targets onto the retina of the patient.

As will be shown hereinafter, to ensure an effective thermal compensation, it is necessary that the photosensitive element 162 is separate from the photosensitive elements 123 but identical to the last-mentioned as regards the operating features.

At the photosensitive element 162, the mask 125 has no through openings for preventing external light sources from disturbing the photosensitive element 162.

If the LED device 161 is also used to project a light target on the retina, the mask 125 advantageously includes a sixth through opening 138 thereat, so as to allow the LED device 161 to emit light toward the beam splitter device 111 (FIGS. 5-6).

Preferably, apparatus 1 comprises second electronic means, operatively associated to the photosensitive element 162 and the control unit 154.

The second electronic means receive the detection signals P2, generated by the photosensitive element 162, and generate second measurement signals Q2, indicative of the light energy $E_2$ received from the latter.

The second electronic means advantageously include an amplifier 156 to amplify the detection signal P2 and an integrator 157 to integrate the output signal from amplifier 156 over time.

When capturing an image of the retina, the thermal calibration unit 160 is not used and the adjustment of the light exposure of the acquisition means is carried out in the same manner as described above, by the light exposure adjustment means, i.e. by the first photosensitive element 123, the first electronic means 151-153 and by the control unit 154.

The detection signals P1 generated by the photosensitive elements 123 are processed by the first electronic means 151-153 generating a measurement signal Q1 indicative of the light energy $E_1$ received from the photosensitive elements 123 and, therefore, indicative of the amount of light reflected by the retina.

The measurement signal Q1 is used by the control unit 154 for controlling the deactivation of illuminator 101, when the light energy $E_1$ received exceeds the predefined threshold $E_{TH}$.

The thermal calibration unit 160 is advantageously used, on the other hand, for performing a thermal calibration process.

Such process is preferably performed by the control unit 154 on a periodic basis, for example every 15 minutes, in the time interval between two successive examinations.

The purpose of the thermal calibration process is to upgrade the threshold value $E_{TH}$ used by the control unit 154 to determine the deactivation of the illumination means 101.

Thus, the control unit 154 may refer to a threshold value $E_{TH}$ that ensures a constant correct light exposure of the acquisition means 110, even in the presence of significant variations in the operating temperature of the photosensitive elements 123.

The above thermal calibration process preferably includes the sequence of steps described below.

Initially, the control unit 154 performs a step I) to power the LED device 161 with a predefined supply current $I_0$ for a predefined supplying time $T_0$.

The control unit 154 then performs a step II) to calculate a new threshold value $E_{NEW}$ to decide the deactivation of the lighting means 101, based on the value of light energy $E_2$ received from the photosensitive element 162.

When the LED device 161 is activated, in fact, the photosensitive element 162 receives the irradiated light thereof and generates a detection signal P2, indicative of the light power received.

The detection signal P2 is amplified by amplifier 156 and integrated over time by integrator 157, thus generating a signal Q2 indicative of the light energy $E_2$ received from the photosensitive element 162.

Based on the value of light energy E2, the control unit 154 can calculate the new threshold value $E_{NEW}$.

The control unit 154 ends the thermal calibration process by storing the new threshold value $E_{NEW}$, thus calculated, as a predefined threshold value $E_{TH}$ to decide the deactivation of the lighting means 101.

In the usage temperature range of apparatus 1, it can be assumed that the amount of light emitted by the LED device 161 only depends on the emission time and on the current wherewith the LED is powered by the control unit 154. The amount of light emitted by a LED device, in fact, depends to a lesser extent on the operating temperature (usually the maximum percentage changes in a temperature range between 15 and 40 degrees, compatible with the operation of the inspection apparatus 1, are about 2%).

Using a predetermined current and supplying time, the amount of light with which the LED device 161 illuminates the photosensitive element 162 is to be considered as a value substantially independently of the operating temperature.

On the other hand, changes in the operating temperature of a photosensitive element determine strong variations in the sensitivity to the light radiation of the latter.

As mentioned above, the photosensitive element 162 is the same type of the photosensitive elements 123 and is substantially at the same temperature as the latter, as it is mounted next to them.

It can therefore be assumed that the variations in the sensitivity to the light radiation of the photosensitive element 162 with temperature substantially correspond to those undergone by the photosensitive elements 123.

During the calibration process, the reference threshold value $E_{TH}$ with which signal Q1 is compared is replaced with a new value $E_{NEW}$ calculated taking into account variations in the sensitivity of the photosensitive element 162 and, therefore, variations in the sensitivity of the photosensitive elements 132.

The effects of variations in the operating temperature on the sensitivity of the photosensitive elements 123 can thus be compensated automatically.

This results in optimal exposure of the images acquired by the acquisition means 110, irrespective of the operating temperature of the apparatus 1.

FIG. 8 shows the apparatus 1, in the embodiment described in FIG. 4, in a calibration configuration. The same calibration configuration can be used for the embodiment of the present invention, which is illustrated in FIG. 1.

When apparatus 1 is in the calibration configuration, a gauge 8 is mounted in front of lens 106 suitable for receiving a light beam 101 from the lighting means 101 and reflecting a portion thereof towards the acquisition means 110.

Preferably, the gauge 8 includes a lens 81 and an artificial retina 82 set up to simulate the internal structure of the patient's eye.

With apparatus 1 in the calibration configuration, the control unit 154 is advantageously able to perform a first calibration process 300 of the light exposure adjustment.

The purpose of this process substantially is to determine the threshold value $E_{TH}$ used by the control unit 154 to decide the deactivation of the lighting means 101 and adjust the light exposure of the acquisition means 110.

The threshold value $E_{TH}$ is determined according to the average brightness value $L_A$ of the images acquired by the acquisition means 110.

Preferably, in said first calibration process, the control unit 154 performs a step i) to activate the lighting means 101 with a predefined light power and for a first activation time The control unit 154 performs a step ii) to store the value $E_1$ of light energy received from the photosensitive elements 123 and a step iii) to store the image acquired by the acquisition means 110.

The control unit 154 then performs a step iv) to calculate the average brightness value $L_A$ of the image stored in step iii) and a subsequent step v) to check whether the average brightness value $L_A$ falls in a range of predefined values L1-L2.

If the average brightness value $L_A$ does not fall within the range of values L1-L2, the calibration process includes a step vi) to repeat the previous steps, varying said first activation time $\tau_1$.

If the average brightness value $L_A$ falls within the range of values L1-L2, the calibration process includes a step vii) to store the value of light energy $E_1$ received from the photosensitive elements 123 as threshold value $E_{TH}$ to be used to decide the deactivation of the lighting means 101.

In said first calibration process of apparatus 1, the lighting means are initially activated for an activation time such that the quick achievement of a correct average brightness value for the images captured by the acquisition means 110 is more likely.

For example, an activation time may be chosen equal to the activation time used to obtain the correct average brightness value in a previous batch of machines.

This significantly reduces the time of the calibration operations for adjusting the light exposure.

This makes it more likely to immediately get a correct average brightness value for the images captured by the acquisition means 110, thus significantly reducing the time of the calibration operations for the light exposure adjustment.

In the presence of the thermal calibration unit 160, as shown in the calibration configuration of FIG. 8, the control unit 154 is advantageously able to perform a second calibration process for the light exposure adjustment.

In this case, the purpose of the calibration process is to determine the predefined current and supply time values $I_0$ and $T_0$ of the LED device 161 to be used during the thermal calibration process described above.

Before starting the second calibration process it is appropriate to wait a sufficiently long time after switching apparatus 1 on to achieve the thermal balance.

In a first step, the second calibration process includes a sequence of steps similar to that described for the first calibration process.

The second calibration process therefore includes:
a step a) to activate the lighting means 101 with a predefined light power and for a second activation time ($\tau_2$);
a step b) to store the value $E_1$ of light energy received from the photosensitive elements 123;
a step c) to store the image acquired by the acquisition means 110;
a step d) to calculate the average brightness value $L_A$ of the image acquired by said acquisition means;
a step e) to check if value $L_A$ falls within a predefined range of values L1-L2;
a step f) to repeat the above steps changing the second activation time $\tau_2$, if the calculated value $L_A$ does not fall within the range of values L1-L2; or
a step g) to store the value $E_1$ of light energy detected as a predefined threshold value $E_{TH}$ to decide the deactivation of the lighting means 101, if value $L_A$ falls within the range L1-L2.

Once the threshold value $E_{TH}$ has been determined, the control unit 154 proceeds to calculate the current and power values of the second LED device 161 based whereon the second photosensitive element receives such light energy $E_2$ as to ensure a threshold value $E_X$ to decide the deactivation of the lighting means 101 that is substantially equal to the threshold value $E_{TH}$.

The second calibration process therefore also includes:
a step h) to power the LED device 161 with a test current $I_{TEST}$ and for a testing time $T_{TEST}$;
a step i) to calculate a threshold value $E_x$ to decide the deactivation of the lighting means 101, based on the value of light energy $E_2$ received from the photosensitive element 162;
a step j) to calculate the absolute value $\Delta_E$ of the difference between value $E_X$ and the predefined threshold value $E_{TH}$. It should be noted that value $\Delta_E$ expresses the absolute error made in calculating value $E_X$;
a step k) to repeat the previous steps h), i) and j), by varying the current or power time $I_{TEST}$ and $T_{TEST}$ of the LED device 161, if value $\Delta_E$ is higher than a predefined value $\Delta_{MAX}$. Of course, value $\Delta_{MAX}$ expresses the maximum permissible error in the calculation of $E_X$;
a step l) to store the values of the test current $I_{TEST}$ and test time $T_{TEST}$ as predefined values $I_0$, $T_0$ to be used in a thermal calibration process, if said $\Delta_E$ is lower than said predefined value $\Delta_{MAX}$.

Both calibration processes described above have the advantage of being performed automatically by the control unit 154. To this end, the digital processing means can run software suitably stored in the memory of the control unit 154.

The operator can thus intervene only to set up the apparatus 1 in the calibration configuration described above.

The above calibration processes can then be completed even by low-skilled staff, limiting in a decisive way the possibility of human errors in the setup operations of apparatus 1.

The calibration processes are particularly suitable to be performed during the industrial production of apparatus 1, and ensure low cost, high accuracy and repeatability of operation.

As shown in FIG. 2-3 or 5-6, mask 124 of the optical unit 120 can be molded in one piece through a molding process, such as injection molding.

In an embodiment variant, illustrated in FIG. 7, mask 124 can be implemented as a stack of shaped plates 124A, each of relatively small thickness.

Plates 124A may advantageously be implemented through an etching process (hardly used with relatively large thickness plates). This type of process can produce complex parts of perforated sheet metal with high precision and is extremely cost efficient, since it requires no appreciable investments to prepare a production line.

For example, the preliminary design and construction of molds are not required, as with injection molding processes.

The apparatus 1, according to the invention, offers significant advantages over the prior art. In the apparatus 1, the optical unit 120 can be integrated the functions of light exposure adjustment of the acquisition means and projection of light targets into a single component. This minimizes noises of the optical light path to the acquisition means 110, resulting in improved contrast and quality of retinal images acquired by the acquisition means 110.

The integrated optical unit further allows obtaining higher performance with regard to the adjustment of the light exposure in the presence of variations in the operating temperature of the photosensitive elements 123, since the thermal calibration unit 160 can effectively compensate for any variations in the sensitivity to light radiation in said photosensitive elements.

In operation, the apparatus 1 can be set up with simple calibration operations and minimum operator intervention, resulting in reduced labor costs.

The apparatus 1 has a very compact structure, with relatively small overall dimensions and weight, and easily manufactured at an industrial level, with significant advantages in terms of reduction of the production costs.

The invention claimed is:

1. Apparatus for inspecting the fundus of the eye, comprising:
    lighting means-configured to project a light beam-for illuminating the retina of one eye; and
    an optical path comprising one or more lenses-configured to optically conjugate the retina with a receiving surface-of acquisition means-configured to acquire one or more images of the retina; and
    a beam splitter device-configured to divert a part-of the light, which is reflected by the retina and directed towards said acquisition means, towards first photosensitive elements; and
    a control unit operatively associated with said first photosensitive elements, said acquisition means and said lighting means, said control unit deactivating said lighting means when the light energy (E1) received from said first photosensitive elements overcomes a predefined threshold value ($E_{TH}$); and
    first LED devices configured to project light targets onto the retina, which the patient must stare to keep the eye still during the examination;
    characterized in that said first photosensitive elements and first LED devices are arranged together in a single integrated optical unit configured to receive light from the retina and to project light onto the retina through said beam splitter device;
    wherein said integrated optical unit includes:
    a support element provided with a mounting surface whereon there are arranged said first photosensitive elements and said first LED devices; and
    a first mask superimposed on said mounting surface, said first mask including first and second through openings, said first through openings being arranged to allow said first photosensitive elements to receive light from said beam splitter device and for optically shielding said first photosensitive elements from other light sources, said second through holes being arranged to allow said first LED devices to emit light towards said beam splitter device and for optically shielding said first LED devices one from each other and from said first photosensitive elements; and
    a second mask superimposed on said first mask and placed on a plane substantially optically conjugated with the retina, said second mask including third and fourth through openings, these third through openings being arranged at said first photosensitive elements to allow said first photosensitive elements to receive light from said beam splitter device, said fourth through holes being arranged at said first LED devices to allow said first LED devices to emit light towards said beam splitter device;
    wherein said integrated optical unit comprises a thermal calibration unit comprising at least one second LED device capable of emitting light towards at least one second photosensitive element and wherein said first mask includes a fifth through opening to shield said second photosensitive element from other light sources.

2. Apparatus, according to claim 1, wherein said integrated optical unit comprises a thermal calibration unit comprising at least one second LED device capable of emitting light towards at least one second photosensitive element.

3. Apparatus, according to claim 1, wherein said control unit performs a thermal calibration process which includes the following steps:
    I) supplying said second LED device with a predefined supply current ($I_0$) and for a predefined supplying time ($T_0$); and
    II) calculating a new threshold value ($E_{NEW}$) to decide the deactivation of said lighting means, based on the value of light energy ($E_2$) received from said second photosensitive element; and
    III) storing said new threshold value ($E_{NEW}$) as the predefined threshold value ($E_{TH}$) to decide the deactivation of said lighting means.

4. Apparatus, according to claim 1, wherein said control unit performs a second calibration process which includes the following steps:
    a) activating said lighting means with a predefined light power and for a second activation time ($\tau_2$); and
    b) storing the value ($E_1$) of light energy received from said first photosensitive elements; and
    c) storing the image acquired by said acquisition means; and
    d) calculating the average brightness value ($L_A$) image acquired by said acquisition means; and
    e) checking whether said average brightness value ($L_A$) falls within a range of predefined values (L1-L2); and
    f) if the calculated average brightness value ($L_A$) does not fall within that predefined range of values (L1-L2), repeating the previous steps by varying said second activation time ($\tau_2$); or
    g) storing the value ($E_1$) of light energy received from the first photosensitive elements as the predefined threshold value ($E_{TH}$) to decide the deactivation of said lighting means, if the calculated average brightness value falls within that predefined range of values; and
    h) supplying said second LED device with a test current ($I_{TEST}$) and for a testing time ($T_{TEST}$); and
    i) calculating a threshold value ($E_X$) to decide the deactivation of said lighting means, based on the value of light energy ($E_2$) received from said second photosensitive element; and
    j) calculating the absolute value ($\Delta_E$) of the difference between the threshold value ($E_X$) calculated at the previous step and the predefined threshold value ($E_{TH}$) to decide the deactivation of said lighting means; and
    k) repeating the previous steps h), i) and j), by varying the current ($I_{TEST}$) or the test time ($T_{TEST}$) used to supply said second LED device, if said absolute value exceeds a preset value ($\Delta_{MAX}$); or
    l) storing the value of the test current ($I_{TEST}$) and test time ($T_{TEST}$) as predefined values ($I_0$, $T_0$) for use in a thermal calibration process, if said absolute value is less than said predefined value ($\Delta_{MAX}$).

5. Apparatus for inspecting the fundus of the eye, comprising:
  lighting means-configured to project a light beam-for illuminating the retina of one eye; and
  an optical path comprising one or more lenses-configured to optically conjugate the retina with a receiving surface-of acquisition means-configured to acquire one or more images of the retina; and
  a beam splitter device-configured to divert a part-of the light, which is reflected by the retina and directed towards said acquisition means, towards first photosensitive elements; and
  a control unit operatively associated with said first photosensitive elements, said acquisition means and said lighting means, said control unit deactivating said lighting means when the light energy (E1) received from said first photosensitive elements overcomes a predefined threshold value ($E_{TH}$); and
  first LED devices configured to project light targets onto the retina, which the patient must stare to keep the eye still during the examination;
  characterized in that said first photosensitive elements and first LED devices are arranged together in a single integrated optical unit configured to receive light from the retina and to project light onto the retina through said beam splitter device;
  wherein said integrated optical unit includes:
    a support element provided with a mounting surface whereon there are arranged said first photosensitive elements and said first LED devices; and
    a first mask superimposed on said mounting surface, said first mask including first and second through openings, said first through openings being arranged to allow said first photosensitive elements to receive light from said beam splitter device and for optically shielding said first photosensitive elements from other light sources, said second through holes being arranged to allow said first LED devices to emit light towards said beam splitter device and for optically shielding said first LED devices one from each other and from said first photosensitive elements; and
    a second mask superimposed on said first mask and placed on a plane substantially optically conjugated with the retina, said second mask including third and fourth through openings, these third through openings being arranged at said first photosensitive elements to allow said first photosensitive elements to receive light from said beam splitter device, said fourth through holes being arranged at said first LED devices to allow said first LED devices to emit light towards said beam splitter device;
  wherein said integrated optical unit comprises a thermal calibration unit comprising at least one second LED device capable of emitting light towards at least one second photosensitive element and wherein said second mask includes a sixth through opening for allowing said second LED device to emit light towards said beam splitter device.

6. Apparatus, according to claim 5, wherein said control unit performs a thermal calibration process which includes the following steps:
  I) supplying said second LED device with a predefined supply current ($I_0$) and for a predefined supplying time ($T_0$); and
  II) calculating a new threshold value ($E_{NEW}$) to decide the deactivation of said lighting means, based on the value of light energy ($E_2$) received from said second photosensitive element; and
  III) storing said new threshold value ($E_{NEW}$) as the predefined threshold value ($E_{TH}$) to decide the deactivation of said lighting means.

7. Apparatus, according to claim 5, wherein said control unit performs a second calibration process which includes the following steps:
  a) activating said lighting means with a predefined light power and for a second activation time ($\tau_2$); and
  b) storing the value ($E_1$) of light energy received from said first photosensitive elements; and
  c) storing the image acquired by said acquisition means; and
  d) calculating the average brightness value ($L_A$) image acquired by said acquisition means; and
  e) checking whether said average brightness value ($L_A$) falls within a range of predefined values (L1-L2); and
  f) if the calculated average brightness value ($L_A$) does not fall within that predefined range of values (L1-L2), repeating the previous steps by varying said second activation time ($\tau_2$); or
  g) storing the value ($E_1$) of light energy received from the first photosensitive elements as the predefined threshold value ($E_{TH}$) to decide the deactivation of said lighting means, if the calculated average brightness value falls within that predefined range of values; and
  h) supplying said second LED device with a test current ($I_{TEST}$) and for a testing time ($T_{TEST}$); and
  i) calculating a threshold value ($E_X$) to decide the deactivation of said lighting means, based on the value of light energy ($E_2$) received from said second photosensitive element; and
  j) calculating the absolute value ($\Delta_E$) of the difference between the threshold value ($E_X$) calculated at the previous step and the predefined threshold value ($E_{TH}$) to decide the deactivation of said lighting means; and
  k) repeating the previous steps h), i) and j), by varying the current ($I_{TEST}$) or the test time ($T_{TEST}$) used to supply said second LED device, if said absolute value exceeds a preset value ($\Delta_{MAX}$); or
  l) storing the value of the test current ($I_{TEST}$) and test time ($T_{TEST}$) as predefined values ($I_0$, $T_0$) for use in a thermal calibration process, if said absolute value is less than said predefined value ($\Delta_{MAX}$).

* * * * *